United States Patent [19]

Yang et al.

[11] 4,302,613
[45] Nov. 24, 1981

[54] INORGANIC CATALYST FOR ALKOXYLATION OF ALCOHOLS

[75] Inventors: Kang Yang; Gerald L. Nield; Paul H. Washecheck, all of Ponca City, Okla.

[73] Assignee: Conoco Inc., Ponca City, Okla.

[21] Appl. No.: 180,236

[22] Filed: Aug. 22, 1980

[51] Int. Cl.³ .............................................. C07C 41/03
[52] U.S. Cl. ..................................... 568/618; 568/616; 568/620; 568/622; 568/623; 568/624; 568/625; 568/678; 568/679
[58] Field of Search ........ 568/616, 618, 620, 622–625, 568/678, 679

[56] References Cited

U.S. PATENT DOCUMENTS 4,223,164 9/1980 Yang et al. .................... 568/678
4,239,917 12/1980 Yang ............................. 568/678

Primary Examiner—Howard T. Mars
Attorney, Agent, or Firm—Cortlan R. Schupbach, Jr.

[57] ABSTRACT

Strontium and barium-based catalyzed alkoxylation of alcohols of all classes is carried out more rapidly and produces a more peaked reaction product when carried out in the presence of co-catalysts such as calcium oxide, calcium carbide, calcium hydroxide, magnesium metal, magnesium hydroxides, zinc oxide, and aluminum metal.

22 Claims, No Drawings

INORGANIC CATALYST FOR ALKOXYLATION OF ALCOHOLS

This invention relates to the production of alkoxylated alcohols by reacting alcohols with an alkoxylating agent in the presence of strontium-containing or barium-containing catalysts and promoters. More particularly, this invention relates to the production of alkoxylated alcohols by reacting said alcohols with alkoxylating agents in the presence of strontium-containing and barium-containing catalysts in the presence of co-catalysts such as calcium carbide, calcium hydroxide, magnesium metal, magnesium hydroxide, zinc oxide, and aluminum metal.

The general reaction of alcohols and adducting materials such as ethylene oxide to form alkoxylated alcohols (ethylene oxide adducts) has long been known and practiced on a commercial scale. For example, ethylene oxide adducts have been used as detergents and cleaning agents, domestic and industrial laundry detergents, detergent builders, polishers, sanitizers, and dry-cleaning materials. Other users include the pulp and paper industry and the fiber industry. These materials are especially adapted to these uses since they have functional properties such as wetting power, foaming, emulsifying and dispersing abilities as well as solubilization and detergent abilities to facilitate their use.

Much literature is available in the general area of ethoxylation of alcohols. Many references are also available relating to the catalytic ability of various materials and the mechanism and kinetics of these reactions. For example, French Pat. No. 1,365,945 teaches the use of compounds containing an active hydrogen atom reacted with ethylene oxide in the presence of an alkali metal base.

Acidic catalysts in general are also known. However, the ethoxylation of alcohols invariably produces a distribution of various adducts. For example on surfactant applications, an adduct of too few ethylene oxide molecules is not effective because of poor solubility. In contrast, an adduct with too many ethylene oxide molecules is likewise undesirable because surface tension reduction per unit mass decreases drastically with increase in the molecular weight. Thus it has long been essential to produce and use ethoxylates with as sharp a distribution in the desired mole adduct range (3 to 10 usually) as possible. Acid-catalyzed reactions produce such alkoxylates but these catalysts produce higher levels of some harmful side products (such as dioxane) which must be separated and removed prior to use.

Russian Pat. No. 523,074 teaches that alkali metals and various carbonates can be used to catalyze these reactions. The side product formation in the base-catalyzed reactions is very low, but in base-catalyzed reactions the adduct distribution is undesirably broad. The result is that a large proportion of the product obtained is not useful or is less desirable because of distribution.

Representative of but not exhaustive of the art in this area is U.S. Pat. No. 3,328,467 which describes the use of zeolites and modified zeolites as catalysts in ethoxylation reactions. French Pat. No. 1,557,407 uses triethyl oxonium fluoroborate to catalyze such reactions. Indeed, the art abounds with references to alkali metal hydroxides such as sodium and potassium hydroxides, tertiary amines and sodium metal. German Offenlegungsschrift No. 2,639,564 teaches polyalkoxylation of active hydrogen compounds in the presence of a sodium fluoroborate or perchlorates of metal such as magnesium, calcium, manganese, or zinc. U.S. Pat. No. 3,969,417 uses tertiary oxonium salts as a catalyst.

U.S. Pat. No. 3,830,850 describes adding sodium, potassium, lithium, rubidium, cesium, calcium, barium, or strontium to condense phenols with formaldehyde, then adding ethylene oxide to the condensation product in an ethoxylation reaction. However, all these materials have the disadvantages described and set forth above.

Great benefit would be provided by a catalyst system which provides the low by-product levels of base catalysts yet has the narrow distribution of the preferred mole adducts obtained from acid catalysts. Such a catalyst which would promote the narrowing of the product distribution curve would contribute significantly to the intrinsic value of the ethoxylate produced. We have described such a catalyst in a copending U.S. application Ser. No. 54,089, filed July 2, 1978. However, this catalyst has an induction period ranging up to about 20 minutes at 178° C. and produces from 1 to 2% polyethylene glycol in the product which while low, is still undesirable.

It is therefore an object of the present invention to provide a catalyst system which will yield a narrow mole adduct distribution from the reaction of alcohols of all classes with materials such as ethylene oxide and propylene oxide while providing low levels of undesirable by-products and unreacted free alcohols, yet provide a reaction which is immediately effective with reduced induction period. Other objects will become apparent to those skilled in this art as the description proceeds.

It has now been discovered according to the present invention that alkoxylation of alcohols of all classes containing from about 4 to about 36 carbon atoms can be carried out by contacting the alcohols with an alkoxylation agent in the presence of at least one catalyst selected from the group consisting of strontium metal, barium metal, strontium hydride, barium hydride, strontium oxide, barium oxide, strontium hydroxide, barium hydroxide, hydrated strontium hydroxide, hydrated barium hydroxide, or mixtures of these together with an effective amount of a co-catalyst promoter or mixture of co-catalyst promoters, wherein the alkoxylation is carried out at temperatures of from about 120° C. to about 260° C. and wherein the co-catalyst promoter is selected from the group consisting of calcium oxide, calcium carbide, calcium hydroxide, hydrated calcium hydroxide, magnesium metal, magnesium hydroxide, hydrated magnesium hydroxide, zinc oxide, and aluminum metal.

Thus, the instant invention provides a method for the alkoxylation of alcohols comprising contacting said alcohols with an alkoxylating agent in the presence of strontium-containing or barium-containing catalysts together with an effective amount of an inorganic co-catalyst to promote the reaction. Normally, the alkoxylation agent will be ethylene oxide or propylene oxide. The instant invention can be carried out at temperatures of from about 90° C. to about 260° C. Normally, the alcohols reactive under the process of the instant invention will contain from about 4 to about 36 carbon atoms but alcohols of from about 4 to about 24 carbon atoms are more common. Those alcohols containing from about 8 to about 18 carbon atoms are most used for commercial processes.

The process of the instant invention can be carried out at ambient pressures. However, pressures of up to 100 pounds per square inch gauge (psig) can also be used. Pressures below about 60 psig are preferred. In addition, pressures below ambient can be used. It is clear that while pressure or lack of pressure is not a detriment to the process of the instant invention, it is simply more convenient to carry out the reaction in the pressure range of from about atmospheric to about 100 psig.

The instant invention is normally carried out at temperatures of from about 120° C. to about 260° C. However, for practical purposes, commercial operations will normally be carried out in the temperature range of from about 150° C. to about 200° C. Temperatures in the range of from 160° C. to about 190° C. are most preferred.

Reactions can be carried out in the presence of any alkoxylation agent which produces a mole adduct of the sort desired. Normally such agents are alpha or beta alkylene oxides. In most commercial operations, either ethylene oxide, propylene oxide, or mixtures of these will be used to produce an adduct. Of these products, ethylene oxide is most preferred.

Reaction products can have any desired content of alkoxylating agent (such as ethylene oxide) but will normally range from about 30% to about 80% based on weight. However, for most purposes, the content of adduct will range from about 40% to about 70% by weight. The amount of adduct present in the reaction is not critical other than the minimum amount necessary to provide sufficient units to reach the mole adduct level desired for the alcohol being reacted.

The strontium-containing and barium-containing catalysts of the present invention are basic catalysts which provide a sharp distribution as to the mole adducts formed, while greatly reducing the amount of unreacted free alcohols and undesirable by-products normally found in sharp distribution reactions. The instant invention adds to these strontium-containing and barium-containing catalysts an effective amount of inorganic co-catalysts in order to further reduce by-product reactions and to reduce or eliminate the induction period necessary for alkoxylation to begin.

Representative examples of strontium-containing catalysts are strontium metal, $SrH_2$, $SrO$, $Sr(OH)_2$ and $Sr(OH)_2 \cdot X\ H_2O$ where X represents the number of water molecules present. Many of these strontium compounds alone are active catalysts and are extremely active catalysts when used with an effective amount of a co-catalyst or promoter.

Representative examples of barium-containing catalysts are barium metal, $BaH_2$, $BaO$, $Ba(OH)_2$ and $Ba(OH)_2 \cdot X\ H_2O$ where X represents the number of water molecules present. Many of these barium compounds alone are active catalysts and are extremely active catalysts when used with an effective amount of a co-catalyst or promoter.

When used, these catalyst mixtures can be used in any desired effective quantity. The larger the quantity used, the more quickly the reaction goes to completion, although larger quantities do not appear to significantly alter the distribution obtained. However, for practical purposes, normally at least about 0.1 weight percent strontium and/or barium catalyst, based upon the weight of the alcohol to be reacted, would be present in the reaction, but from 0.1 to 5.0 weight percent is more commonly used and 0.1 to 2.0 weight percent is preferred. The amount of promoter or co-catalyst which should be present with the strontium or barium catalyst is generally an effective amount. The effect of the co-catalyst or promoter becomes significant at about 0.1% by weight based upon the weight of the alcohol to be reacted. It is logical to expect an upper limit after which the amount of promoter present will produce no additional benefits.

Normally, these materials will be added to the strontium or barium catalysts in amounts ranging from about 0.1 to about 2% by weight based upon the weight of the alcohol. Although amounts ranging from about 0.15 to about 1.5 are preferred, and amounts ranging from about 0.3 to about 0.8% by weight based upon the weight of alcohol to be reacted is most preferred. However, it is very apparent that these limits can be varied substantially. It may be advantageous to preform or prereact the inorganic promoter with the catalyst prior to addition to the alkoxylation system. To effect such prereaction, the desired amount of catalyst is reacted with an effective amount of promoter for a period of time ranging up to about 4 hours at temperatures up to about 200° C. Preferred conditions are 25° C. to about 160° C. for up to about 2.5 hours. Such preformed catalysts can be isolated or, preferably, added as a reaction mixture to the alkoxylation reaction.

The instant invention is effective with all classes of alcohols, both saturated and unsaturated. Representative examples of both unsaturated and saturated alcohols are set forth below.

The instant invention is effective with all classes of unsaturated alcohols. Representative examples of such alcohols are acetylenic alcohols. These alcohols include hexynols such as 1-hexyn-3-ol, ethyloctynols such as 4-ethyl-1-octyn-3-ol, methylbutynols such as 2-methyl-3-butyn-2-ol and methylpentynols such as 3-methyl-1-pentyn-3-ol. Other alcohols include cis-9-octadecen-1-ol, 2,5-dimethyl-3-hexyne-2,5-diol, 3,6-dimethyl-4-octyne-3,6-diol and 2,4,7,9-tetramethyl-5-decyne-4,7-diol.

While the instant invention is effective with all classes of alcohols, alkanols are preferred. Of the alkanols, which include both linear and branched primary and secondary alkanols, the linear and branched primary alkanols are the most commonly used and are the preferred alcohols of the instant invention. Representative examples of such alcohols are those derived by hydrogenation of natural fats and oils, such as CO and TA alcohols, trademark of and sold by Proctor and Gamble Co., such as CO-1214 N alcohol, CO-1618 alcohol, and TA 1618 alcohol, and ADOL alcohols, trademark of and sold by Ashland Oil Co., such as ADOL 54 alcohol, ADOL 61 alcohol, ADOL 64 alcohol, ADOL 60 alcohol and ADOL 66 alcohol. Alcohols produced by Ziegler chemistry can also be ethoxylated. Examples of these alcohols are ALFOL alcohols, trademark of and sold by Conoco Inc, such as ALFOL 1012 alcohol, ALFOL 1214 alcohol, ALFOL 1412 alcohol, ALFOL 1618 alcohol, ALFOL 1620 alcohol; and EPAL alcohols, trademark of and sold by Ethyl Chemical Co., such as EPAL 1012 alcohol, EPAL 1214 alcohol, EPAL 1418 alcohol. The invention is extremely useful for oxo alcohols (hydroformylation) produced from olefins. Examples of such alcohols are NEODOL alcohol, trademark of and sold by Shell Oil Co., such as NEODOL 23 alcohol, NEODOL 25 alcohol, NEODOL 45 alcohol; TERGITOL-L, trademark of Union Carbide Corp., such as TERGITOL-L 125 alcohol;

LIAL alcohols, trademark of and sold by Liquichimica Co. such as LIAL 125; and isodecyl and tridecyl alcohols, sold by Exxon Corp., such as isodecyl alcohol and tridecyl alcohol. Guerbet alcohols can also be alkoxylated. Representative examples of these alcohols are STANDAMUL alcohols, trademark of and sold by Henkel Chemical Co., such as STANDAMUL GT-12 alcohol, STANDAMUL GT-16 alcohol, STANDAMUL GT-20 alcohol, STANDAMUL GT-1620 alcohol. Secondary alcohols can also be used, such as TERGITOL 15 alcohol, trademark of and sold by Union Carbide Corp.

Representative examples of such alcohols are 1-decanol; 1-undecanol; 1-dodecanol; 1-tridecanol; 1-tetradecanol; 1-pentadecanol; 1-hexadecanol; 1-heptadecanol; 1-octadecanol; 1-nonadecanol; 1-eicosanol; 1-docosanol; 2-methyl-1-undecanol; 2-propyl-1-nonanol; 2-butyl-1-octanol; 2-methyl-1-tridecanol; 2-ethyl-1-dodecanol; 2-propyl-1-undecanol; 2-butyl-1-decanol; 2-pentyl-1-nonanol; 2-hexyl-1-octanol; 2-methyl-1-pentadecanol; 2-ethyl-1-tetradecanol; 2-propyl-1-tridecanol; 2-butyl-1-dodecanol; 2-pentyl-1-undecanol; 2-hexyl-1-decanol; 2-heptyl-1-decanol; 2-hexyl-1-nonanol; 2-octyl-1-octanol; 2-methyl-1-heptadecanol; 2-ethyl-1-hexadecanol; 2-propyl-1-pentadecanol; 2-butyl-1-tetradecanol; 1-pentyl-1-tridecanol; 2-hexyl-1-dodecanol; 2-octyl-1-decanol; 2-nonyl-1-nonanol; 2-dodecanol; 3-dodecanol; 4-dodecanol; 5-dodecanol; 6-dodecanol; 2-tetra-decanol; 3-tetradecanol; 4-tetradecanol; 5-tetradecanol; 6-tetradecanol; 7-tetradecanol; 2-hexadecanol; 3-hexadecanol; 4-hexadecanol; 5-hexadecanol; 6-hexadecanol; 7-hexadecanol; 8-hexadecanol; 2-octadecanol; 3-octadecanol; 4-octadecanol; 5-octadecanol; 6-octadecanol; 7-octadecanol; 8-octadecanol; 9-octadecanol; 9-octadecanol-1; 2,4,6-trimethyl-1-heptanol; 2,4,6,8-tetramethyl-1-nonanol; 3,5,5-trimethyl-1-hexanol; 3,5,5,7,7-pentamethyl-1-octanol; 3-butyl-1-nonanol; 3-butyl-1-undecanol; 3-hexyl-1-undecanol; 3-hexyl-1-tridecanol; 3-octyl-1-tridecanol; 2-methyl-2-undecanol; 3-methyl-3-undecanol; 4-methyl-4-undecanol; 2-methyl-2-tridecanol; 3-methyl-3-tridecanol; 4-methyl-3-tridecanol; 4-methyl-4-tridecanol; 3-ethyl-3-decanol; 3-ethyl-3-dodecanol; 2,4,6,8-tetramethyl-2-nonanol; 2-methyl-3-undecanol; 2-methyl-4-undecanol; 4-methyl-2-undecanol; 5-methyl-2-undecanol; 4-ethyl-2-decanol; 4-ethyl-3-decanol; tetracosanol; hexacosanol; octacosanol; triacontanol; dotriacontanol; hexatriacontanol; 2-decyltetradecanol; 2-dodecylhexadecanol; 2-tetradecyloctadecanol; 2-hexadecyleicosanol.

The catalysts and method of the present invention are extremely well suited for the alkoxylation of alcohols produced by olefins by hydroformylation (or oxo/hydrogenation). Such alcohols have, in the past, presented difficulty when used as reactants for alkoxylation and particularly ethoxylation because of the high concentration of unreacted alcohols. The catalysts of the present invention produce extremely good ethoxylates using these alcohols.

The instant invention provides a method for obtaining high mole adduct alkoxylates of alcohols having a very narrow, highly desirable distribution range. In addition, the products have low amounts of by-products and unreacted free alcohols together with a desirably fast reaction rate. The inorganic co-catalysts or promoters of the present invention greatly reduce the previously noted induction period present with these catalysts.

Generally, the treatment of alcohols with ethylene oxide yields a non-ionic detergent since hydrogen bonding to the numerous oxygen atoms makes the polyether end of the molecule water soluble. Alternatively, the ethoxylates can be converted into sulfates and used in the form of alkali metal or ammonium salts.

The instant invention provides for the production of highly efficient alcohol alkoxylates from primary and secondary branched chain and straight chain alcohols in a novel, highly unexpected manner. Of these, primary alkanols are preferred. These alcohols normally have from about 4 to about 20 carbon atoms, but from about 4 to about 36 carbon atoms can also be used. Reaction products are useful as non-ionic surface active agents with high wetting power and are composed with mixtures of mono-alkyl ethers of polyethylene glycol.

Thus, in the preferred form of the instant invention, ethylene oxide is reacted with a branched chain or straight chain higher alkanol in the presence of barium or strontium metal, barium or strontium hydride, barium or strontium oxide, barium or strontium hydroxide, or other barium and strontium bases promoted by an effective amount of at least one material selected from the group consisting of CaO, Ca(OH)$_2$, Mg, Mg(OH)$_2$, ZnO, CaC$_2$ and Al.

The invention is more concretely described with reference to the examples below wherein all parts and percentages are by weight unless otherwise specified. The examples are provided to illustrate the instant invention and not to limit it.

Although exemplified as a batch reaction, the catalysts and promoters of the present invention are extremely well suited to continuous reaction methods. The reaction products are of extremely high quality and quantity.

EXAMPLE 1

(comparative example)

A stainless steel reactor was charged with 1.0 grams strontium hydroxide.8H$_2$O and 180 grams ALFOL 1412 alcohol (alcohol derived from the hydrolysis of aluminum alkoxides containing 12 to 14 carbon atoms, Trademark of and sold by Conoco Inc.) After purging with nitrogen at 250 cubic centimeters (cc) per minute at 150° C. for 30 minutes, the temperature was raised to 178° C. The reactor was briefly evacuated and ethylene oxide was charged to a pressure of about 40 pounds per square inch gauge (psig). No appreciable reaction occurred in 120 minutes.

EXAMPLE 2

An experiment was carried out as described in Example 1 except that 3.0 grams of calcium oxide was added as a co-catalyst. In 78 minutes 120 grams of ethylene oxide had reacted, producing an ethoxylate containing 10.5% free alcohol.

EXAMPLE 3

An experiment was carried out as described in Example 2 except that 0.5 g barium hydroxide .8H$_2$O was used instead of Sr(OH)$_2$.8H$_2$O. In 60 minutes, 120 g of ethylene oxide had reacted, producing an ethoxylate containing 10% free alcohol.

EXAMPLE 4

An experiment was carried out as described in Example 1 except that 3.0 grams of magnesium oxide was added as a co-catalyst. In 88 minutes 120 grams of ethylene oxide was reacted producing an ethoxylate containing 9.7% free alcohol.

EXAMPLE 5

An experiment was carried out as described in Example 1 except that 1.0 gram of powdered magnesium metal was used as a co-catalyst. In 106 minutes 120 grams of ethylene oxide was reacted producing an ethoxylate containing 10.0% free alcohol.

EXAMPLE 6

An experiment was carried out as described in Example 1 except that 1.0 grams of calcium carbide ($CaC_2$) was added as a co-catalyst. In 73 minutes 120 grams of ethylene oxide reacted producing an ethoxylate containing 10.0% free alcohol.

Example 7

An experiment was carried out as described in Example 1 except that 3.0 grams zinc oxide as added as a co-catalyst. In 90 minutes 120 grams of ethylene oxide reacted, producing an ethoxylate containing 10.2% free alcohol.

EXAMPLE 8

An experiment was carried out as described in Example 1, except that 0.5 gram of aluminum powder was added as a co-catalyst. In 111 minutes 120 g of ethylene oxide reacted, producing an ethoxylate containing 9.8% free alcohol.

While certain embodiments and details have been shown for the purpose of illustrating this invention, it will be apparent to those skilled in this art that various changes and modifications may be made herein without departing from the spirit or scope of the invention.

We claim:

1. A method for the alkoxylation of alcohols containing from about 2 to about 36 carbon atoms, comprising carrying out said alkoxylation by contacting said alcohols with an alkoxylating agent in the presence of basic strontium-containing or barium-containing materials together with an effective amount of an inorganic co-catalyst selected from the group consisting of calcium oxide, calcium carbide, calcium hydroxide, magnesium metal, aluminum metal, zinc oxide, and magnesium hydroxide, and wherein the alkoxylation reaction is carried out at temperatures of from about 120° C. to about 260° C.

2. A method as described in claim 1 wherein the alkoxylation is carried out using ethylene oxide, propylene oxide, or mixtures of these.

3. A method as described in claim 2 wherein the catalyst is selected from the group consisting of strontium metal, strontium hydride, strontium hydroxide, hydrated strontium hydroxide, or strontium oxide.

4. A method as described in claim 3 wherein the reaction is carried out at a pressure of up to about 100 pounds per square inch gauge.

5. A method as described in claim 4 wherein ethylene oxide is used as the alkoxylation agent and a mole adduct ratio ranging from about 30 weight percent to about 80 weight percent of the ethoxylated product is recovered.

6. A method as described in claim 5 wherein the alcohol is an alkanol containing from about 4 to about 36 carbon atoms.

7. A method as described in claim 6 wherein the strontium-containing catalyst is present in an amount of at least about 0.1% by weight based upon the alcohol to be reacted.

8. A method as described in claim 7 wherein the alcohol to be ethoxylated contains from about 4 to about 20 carbon atoms.

9. A method as described in claim 8 wherein the alcohol is a primary alcohol.

10. A method as described in claim 8 wherein the alcohol is the product of a hydroformylation/hydrogenation reaction.

11. A method as described in claim 7 when carried out in a continuous fashion.

12. A method as described in claim 7 wherein the catalyst is pre-formed prior to alkoxylation.

13. A method as described in claim 2 wherein the catalyst is selected from the group consisting of barium metal, barium hydride, barium hydroxide, hydrated barium hydroxide, or barium oxide.

14. A method as described in claim 13 wherein the reaction is carried out at a pressure of up to about 100 pounds per square inch gauge.

15. A method as described in claim 14 wherein ethylene oxide is used as the alkoxylation agent and a mole adduct ratio ranging from about 30 weight percent to about 80 weight percent of the ethoxylated product is recovered.

16. A method as described in claim 15 wherein the alcohol is an alkanol containing from about 4 to about 36 carbon atoms.

17. A method as described in claim 16 wherein the barium-containing catalyst is present in an amount of at least about 0.1% by weight based upon the alcohol to be reacted.

18. A method as described in claim 17 wherein the alcohol to be ethoxylated contains from about 4 to about 20 carbon atoms.

19. A method as described in claim 18 wherein the alcohol is a primary alcohol.

20. A method as described in claim 18 wherein the alcohol is the product of a hydroformylation/hydrogenation reaction.

21. A method as described in claim 17 when carried out in a continuous fashion.

22. A method as described in claim 17 wherein the catalyst is pre-formed prior to alkoxylation.

* * * * *